United States Patent [19]

Buchwald et al.

[11] Patent Number: 5,292,893
[45] Date of Patent: Mar. 8, 1994

[54] CATALYTIC ASYMMETRIC AND NON-ASYMMETRIC REDUCTION OF TIMES AND OXIMES USING METAL CATALYSTS

[75] Inventors: Stephen L. Buchwald; Christopher A. Willoughby, both of Somerville, Mass.

[73] Assignee: Massachusetts Institute of Technology, Cambridge, Mass.

[21] Appl. No.: 792,229

[22] Filed: Nov. 14, 1991

Related U.S. Application Data

[63] Continuation-in-part of Ser. No. 698,940, May 13, 1991, abandoned, which is a continuation-in-part of Ser. No. 616,892, Nov. 21, 1990.

[51] Int. Cl.$^5$ ................. C07D 207/02; C07D 307/02; C07D 207/06; C07C 209/40; C07C 209/52
[52] U.S. Cl. ..................... 548/577; 548/579; 549/491; 564/302; 564/303; 564/304; 564/305; 564/355; 564/356; 564/374; 564/375; 564/378; 564/385; 564/392; 564/415
[58] Field of Search ............. 564/305, 698, 940, 616, 564/892, 375, 415, 448, 489, 302, 303, 304, 355, 356, 374, 385, 392; 548/577, 576; 549/491

[56] References Cited

U.S. PATENT DOCUMENTS

| | | | |
|---|---|---|---|
| 1,845,280 | 2/1932 | Jager | 564/489 X |
| 3,412,174 | 11/1968 | Kroll | 564/448 X |
| 3,873,621 | 3/1975 | Kreevoy et al. | 564/489 X |
| 3,932,534 | 1/1976 | Fukunaga et al. | 564/415 X |
| 4,078,002 | 3/1978 | Brown | 564/415 X |
| 4,372,893 | 2/1983 | Eckert | 564/415 X |
| 4,532,351 | 7/1985 | Barnett et al. | 564/415 |
| 4,985,567 | 1/1991 | Achiwa et al. | 564/415 X |

FOREIGN PATENT DOCUMENTS

| | | | |
|---|---|---|---|
| 0051803 | 5/1982 | European Pat. Off. | 564/415 |
| 0302021 | 2/1989 | European Pat. Off. | 564/415 |

OTHER PUBLICATIONS

Hajos, "Studies in Organic Chemistry 1, Complex Hydrides and Related Agents in Organic Synthesis", pp. 190 to 193 (1979).

Nicolaou et al, Angew. Chem. Int Ed. Eng, vol. 30, pp. 585–588 (1991).

Iridium (III) Hydride Complexes for the Catalytic Enantioselective Hydrogenation Of Imines, Chan et al. (J. Am. Chem. Soc., 1990, 112, 9400).

Enantioselektive Hydrosilylierung von prochiralen 3,4–Dihydro-2H-pyrrol-Derivaten Becker et al. (Angew. Chem., 1985, 93, 969).

Organocerium Additions to SAMP-Hydrazones: General Synthesis of Chiral Amines Denmark et al. (J. Am. Chem. Soc., 1987, 109, 2224).

(List continued on next page.)

*Primary Examiner*—Floyd D. Higel
*Attorney, Agent, or Firm*—Thomas J. Engellenner; William C. Geary, III

[57] ABSTRACT

A process is provided for catalytically reducing imines, oximes, hydrazones and related compounds. Moreover, there is provided a process for the catalytic asymmetric reduction of imines, oximes, hydrazones, and the like, using enantiomerically enriched catalysts, to provide chiral amine reaction products which are enriched in one enantiomer. Catalytic asymmetric reduction can also be carried out using an achiral precatalyst in combination with an optically active additive. These reduction reactions can be carried out in the presence of an inert gas or in an atmosphere of hydrogen, where hydrogen is the stoichiometric reducing agent. An active species of a catalyst useful with the invention is selected from the group consisting of $M(L)(L')(L'')$, $M(L)(L')(L'')(L''')$, $M(L)(L')(L'')(L''')(L^{iv})$, and $M(L)(L')(L'')(L''')(L^{iv})(L^{v})$, where M is a group 3, 4, 5 or 6 metal, a lanthanide or an actinide, and L, L', L'', L''', $L^{iv}$, $L^{v}$, independently, is a combination of H, alkyl, aryl, $Si(R)(R')(R'')$, halogen —OR, —SR, or —NR(R') or a cyclopentadienyl group.

45 Claims, No Drawings

OTHER PUBLICATIONS

Chiral Toluene-2,x-Sultam Auxiliaries: Preparation and Structure of Enantiomerically Pure (R)- and (S)-Ethyl-2,1'-Sultam[1], Oppolzer et al. (Tetrahedron Lett., 1990, 31, 4117).

Asymmetric Hydrosilylation of a Schiff Base of Acetophenone Catalyzed by Rh(AMPP) Complexes, Kokel et al. (J. Mol. Cat., 1989, 57, L5-L7).

Asymmetric Homogeneous Hydrogenation of Imines Using Rhodium-Phosphine Systems, Cullen et al. (J. Mol. Cat., 1990; 62, 243).

Novel Diphosphinoiridium Catalysts for the Enantioselective Hydrogenation of N-Arylketimines, Spindler et al. (Angew. Chem. Int. Ed. Eng., 1990, 29, 558).

Rhodium(l)-catalysed Asymmetric Hydrogenation of Imines, Kang et al. (J. Organomet. Chem., 1975, 90, 353).

Reduction Asymetrique Catalysee Par Des Complexes De Metaux De Transition, Kagan et al. (J. Organomet. Chem., 1975, 90, 353).

Synthesis and Molecular Structures of Chiral Titanocene Derivatives with Bridged Tetrahydroindenyl Ligands, Wild et al. (J. Organomet. Chem., 1982, 232, 233).

Enantioselective hydrosilylation of ketones by diphenylsilane with RH (cod)$Cl_2$/pyridinethiazolidine Catalysts, Brunner et al. (J. Organomet. Chem., 1988, 346, 413).

Rhodium Phosphine Complexes as Homogeneous Catalysts. 14. Asymmetric Hydrogenation of a Schiff Base of Acetophenone-Effect of Phosphine and Catalyst Structure on Enantioselectivity, Vastag et al. (J. Mol. Cat. 1984, 22, 283).

Catalytic and structural studies of $RH^1$ complexes of (−) (2S,4S)-2,4-bis (diphenylphosphino)pentane. Asymmetric hydrogenation of acetophenonebenzylimine and acetophenone, Bakos et al. (J. Organomet. Chem., 1989; 370, 263).

Diastereomeric Derivatisation and Enantiomer Separation of Ethylenebis (Tetrahydroindenyl)-Titanium and -Zirconium Dichlorides, Schafer et al. (J. Organomet. Chem., 1987, 328, 87).

CATALYTIC ASYMMETRIC AND NON-ASYMMETRIC REDUCTION OF TIMES AND OXIMES USING METAL CATALYSTS

The U.S. Government has rights in this invention pursuant to NIH Grant Number GM 34917.

REFERENCE TO RELATED APPLICATION

This is a continuation-in-part of U.S. patent application Ser. No. 698,940, filed May 13, 1991, entitled "Catalytic Asymmetric Reduction of Imines and Oximes", and now abandoned, which is a continuation-in-part application of U.S. patent application Ser. No. 616,892 filed Nov. 21, 1990, entitled "Catalytic Reduction of Organic Carbonyls".

BACKGROUND OF THE INVENTION

The present invention relates to processes for catalytically reducing and/or transforming imines, oximes, hydrazones, and the like, and for the catalytic asymmetric reduction of such compounds.

Reactions which reduce imines, oximes, hydrazones and the like, often are commercially quite significant, as they can be used in the large scale preparation of pharmaceuticals and specialty chemicals. Thus, the safety and economy of the reduction reactions are important considerations. Processes which safely and economically produce amines are of great interest since these compounds are widely used as pharmaceuticals and specialty chemicals. Moreover, many pharmaceutically active amines are optically active compounds, and effective processes for generating amines enriched in a desired enantiomer are thus needed. Currently utilized methods of producing enantiomerically enriched amines rely upon the use of expensive late transition metal catalysts and potentially hazardous reagents.

Accordingly, it would be advantageous to provide safer and more economical processes for reducing compounds such as imines, oximes, hydrazones and the like.

It is thus an object of the invention to provide a safer and more economical process for catalytically reducing compounds such as imines, oximes, and hydrazones. Another object is to provide such a reaction where the end product of the reaction is effectively and conveniently isolated. A further object is to provide safe and economical processes for preparing chiral amines, enriched in one enantiomer, by the catalytic asymmetric reduction of imines, oximes, hydrazones, and the like. Other objects will be apparent upon reading the disclosure which follows.

SUMMARY OF THE INVENTION

The disclosure of the related parent applications, U.S. patent application Ser. No. 698,940, filed May 13, 1991, entitled "Catalytic Asymmetric Reduction of Imines and Oximes", and U.S. patent application Ser. No. 616,892, filed Nov. 21, 1990, entitled "Catalytic Reduction of Organic Carbonyls", are both hereby incorporated by reference.

Unless otherwise clear from its context, the term "catalyst" is used interchangeably herein to refer both to the metal complexes or precatalysts before their activation as catalytic species, and to the active catalytic species themselves. With respect to the embodiment of the invention which utilizes an achiral "catalyst" in combination with an optically active additive, the complex added to the reaction mixture is referred to herein as a "catalyst", even though the actual catalytic entity may not be formed until after activation of the complex and/or combination of the chiral additive and the complex.

The invention provides a relatively safe and effective catalytic process for conveniently reducing imines, oximes, hydrazones and the like. The catalytic asymmetric reduction of such compounds to yield chiral amines enriched in one enantiomer provides another aspect of the invention. The term "imines" is sometimes used in this specification to refer collectively to imines, oximes, hydrazones and related compounds.

Generally, the process of the invention involves first generating an active species of an effective reduction catalyst which is used in the reaction. Where catalytic asymmetric reduction is to occur, the catalyst can be a chiral non-racemic catalyst, enriched in one enantiomer. In another embodiment of the invention an achiral precatalyst, in combination with an optically active additive, may be used to effect asymmetric reduction. In one embodiment, the catalyst is a titanium-containing complex, however, other catalysts may be used as well.

Formation of the active catalyst (where necessary) is effected by subjecting a catalytic amount (i.e., about 3 to 10 percent by mole) of the pre-catalyst (e.g., a titanium containing complex) to between 1 and 2 equivalents of an alkylating or reducing agent, relative to the pre-catalyst. A stoichiometric amount of a silane reducing reagent is then combined with a catalytic amount (i.e., about 3 to 10 percent by mole) of the catalyst. The desired imine substrate is then allowed to react with the silane reagent in the presence of the catalyst.

The reduction of imines and related compounds by this reaction yields a silicon-containing intermediate when a silane serves as the reducing agent. Silicon is cleaved from the intermediate by conventional techniques, after quenching of the catalyst, to yield a crude end product in a more reduced form than the starting compound. The end Product may then be purified by known techniques.

In one embodiment, as noted above, a silane compound acts as the reducing agent and the reduction reaction can be carried out in an inert gas such as argon or nitrogen.

The process of the invention can also be carried out where hydrogen, rather than a silane, serves as the reducing agent. In such an embodiment the active catalytic species can be generated in the presence of a silane compound and an inert gas. Thereafter, the reduction reaction takes place in the presence of hydrogen which is present in excess and is the stoichiometric reductant. Reduction reactions carried out in this way do not require a silicon cleavage step. Following the reduction reaction one need only perform conventional separation and purification techniques to yield the desired end product.

Catalytic asymmetric reduction may also be accomplished through another method which involves using an optically active additive in combination with the precatalyst, reductant and substrate. In this embodiment the precatalyst may be chiral or achiral, and the reducing agent may be a silane or hydrogen.

DETAILED DESCRIPTION OF THE INVENTION

The process of the invention can be used to effect the catalytic asymmetric reduction of imines, oximes, hydrazones and related compounds such as oxime O-alkyl ethers, oxime O-aryl ethers, N,N-dialkylhydrazones, N,N-diarylhydrazones, and N-alkyl-N-arylhydrazones, to yield amines which are enriched in one enantiomer. Alternatively, these substrates may also be catalytically reduced, non-asymmetrically, to yield amines. For catalytic asymmetric reduction reactions, the catalyst can be one which is enriched in one enantiomer. Generally, an enantiomerically enriched catalyst is one which has more than 50 percent of one enantiomer. More specifically, an enantiomerically enriched catalyst is one which preferably has greater than 80%, and most preferably greater than 90%, of one enantiomer.

Catalytic asymmetric reduction can also be carried out using an achiral precatalyst in combination with an optically active additive.

The basic steps of the invention involve first generating an active species of an effective catalyst which, depending upon the identity of the catalyst, may be dispensed in an organic solvent such as tetrahydrofuran, ether, toluene, benzene, hexane, or the like. Preferably, this mixture is maintained in an atmosphere of an inert gas such as argon or nitrogen within which the reduction reaction takes place. In some instances, especially where certain titanium-containing catalysts are used as explained below in more detail, the catalyst is activated by dissolving the catalyst in a solvent together with an alkylating or reducing agent.

Once the active catalyst is formed, it can be mixed with a silane reducing reagent which provides the source of hydride ion for the reduction reaction. Usually, the catalyst-solvent mixture is maintained at a relatively low temperature (e.g., between about −60° C. to −78° C.) until it is mixed with the silane. Thereafter, the mixture may be allowed to warm to between about 0° C. and room temperature. It is noted, however, that the catalyst may also be generated at room temperature. The imine substrate is then reacted, at a temperature between about room temperature and 100° C., with the silane reagent in the presence of the activated catalyst. Typically, the reaction requires from about 15 minutes to 48 hours to complete. The reaction can be terminated by deactivating the catalyst through exposure to air.

As an alternative to the reduction reaction procedure described above, hydrogen can be used as the reducing agent instead of the silane compound. In this embodiment the active catalyst may be generated, as discussed above, in an inert gas. After adding the substrate to the silane and catalyst the reactants may be transferred to a reaction vessel which is able to be charged with hydrogen at ambient or elevated pressures.

Where the reaction is to be conducted using a hydrogen reducing agent at high pressure, the reactant-catalyst mixture can be transferred to a suitable pressure reactor prior to commencing the reaction, in a manner such as described below. Once the substrate is added to the vessel containing active catalyst and silane (in an inert gas), the vessel is sealed and moved into a dry box. The reaction mixture can then be transferred to a high pressure reactor (such as a Parr high pressure reactor) where it is removed from the dry box. The reactor is then charged with hydrogen and the reaction commences upon heating to between 25°–100° C. The reaction can be conducted in hydrogen at a pressure ranging from 1 atmosphere to over 2000 psi.

In the embodiment in which hydrogen serves as the reducing agent, it is preferable to use between about 0.1–10% by mole of catalyst relative to the substrate, and more preferably, between about 5–10% by mole of catalyst relative to the substrate.

When a silane is used as the reducing agent the reduction reaction yields a silicon-containing intermediate compound. The silicon may be cleaved from the intermediate by hydrolysis or alcoholysis, and a variety of known extraction techniques may be employed to isolate the desired end product of the reduction reaction. For example, silicon cleavage may be effected by treatment with alcoholic or aqueous solutions (or mixed alcohol/aqueous solutions) of acids or bases such as hydrochloric acid or sodium hydroxide. Alternatively, silicon cleavage may be effected by the addition of an alcohol, such as methanol or ethanol, or a mixed alcohol/water solution. Subsequently, extraction, separation and drying techniques can be utilized to recover the crude product, which can then be purified by a conventional technique such as chromatography. The reduction reaction does not require a silicon cleavage step when hydrogen is used as the reducing agent. However, separation and purification techniques generally must be effected to recover the desired end product.

A variety of precatalysts can be used effectively in the reduction reactions of the present invention. Exemplary precatalysts broadly include those having the general formulas:

 (1)

 (2)

 (3)

 (4)

wherein M is a group 3, 4, 5 or 6 metal, a lanthanide, or an actinide and where L, L', L", and L'", L$^{iv}$ and L$^v$, independently, can be some combination of H, an alkyl group, an aryl group, a cyclopentadienyl group, Si(R)(R')(R"), a halogen, —OR, —SR, or -NR(R'), where R, and R' and R" may be H, an alkyl, aryl, or silyl group and may be different or the same. A cyclopentadienyl group (designated "Cp") is represented by the formula

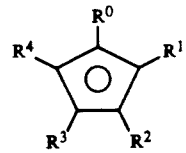

where R$^0$, R$^1$, R$^2$, R$^3$, and R$^4$ may be hydrogen, alkyl, aryl, trialkylsilyl, triarylsilyl, (dialkyl)arylsilyl, or (diaryl)alkylsilyl groups in any combination and may all be the same or different. Examples of group 3, 4, 5 or 6 metals which may be useful with the present invention include titanium, vanadium, niobium, chromium yttrium, scandium, and lanthanum. Examples of useful lanthanides include samarium, ytterbium, and lutetium. Examples of useful actinides include thorium and uranium. Titanium, however, is the most preferred metal.

One preferred titanium-containing catalyst is titanocene dichloride which is represented by the formula

wherein Cp represents a $\eta^5$-cyclopentadienyl group. Alternatively, titanocene monochloride (Cp$_2$TiCl) may be used as a catalyst as well. Another preferred titanium-containing catalyst has the general formula $$Cp_2Ti(OR)(OR')$$

where R and R' can be alkyl, aryl, silyl or hydrogen and can be the same or different.

An additional preferred catalyst, which is particularly useful in conducting catalytic asymmetric reduction reactions is generally represented by the formula $$YTiX_2$$

where Y represents ethylene-1,2-bis ($\eta^5$-4,5,6,7-tetrahydroindenyl), and X represents groups including halides, alkoxides, amides, sulfides, alkyls, aryls, hydrides, and tri-substituted silyls. Catalysts having the ethylene-1,2-bis($\eta^5$-4,5,6,7-tetrahydroindenyl backbone are referred to herein as "BIE" catalysts. In a preferred embodiment X$_2$ represents 1,1'-binaphth-2,2'-diolate. Specific preferred catalysts for asymmetric reduction thus include (R,R)-Ethylene-1,2-bis($\eta^5$-4,5,6,7-tetrahydroindenyl) titanium (R)-1,1'-binaphth-2,2'-diolate and (S,S)-Ethylene-1,2-bis($\eta^5$-4,5,6,7-tetrahydroindenyl) titanium (S)-1,1'-binaphth-2,2'-diolate.

When a BIE-type catalyst is used for catalytic asymmetric reduction reactions, it preferably is enriched in one enantiomer of the molecule. Generally, enantiomeric enrichment requires more than 50% of one enantiomer, but more specifically requires more than 80% of one enantiomer. In a Preferred embodiment, an enantiomerically enriched catalyst has more than 90% of one enantiomer. Of course, the greater the level of enantiomeric purity of the catalyst, the greater will be the enantiomeric purity of the end product of the reaction.

Other preferred catalysts include metal alkoxides and metal aryloxides such as titanium alkoxides and titanium (IV) aryloxides. Specific catalysts include titanium (IV) isopropoxide, titanium (IV) ethoxide, and trichlorotitanium (IV) isopropoxide, titanium (IV) methoxide, and titanium (IV) butoxide. Of these, the most preferred catalysts include titanium (IV) isopropoxide, titanium (IV) ethoxide and trichlorotitanium (IV) isopropoxide.

The catalysts useful in this invention may be active as electronically neutral molecules, anions or cations.

The titanocene dichloride, titanocene monochloride and BIE catalysts must be activated by reaction with an alkylating agent or reducing agent, preferably in an organic solvent. Suitable alkylating agents are known to those skilled in the art and generally include organometallic compounds. Examples of such compounds include alkylmagnesium halides, alkyllithium compounds, alkylaluminum compounds and boron, aluminum, or other metal alkyls or metal hydrides. Particularly preferred alkylating agents include n-pentylmagnesium bromide, n-butyllithium, and sodium acetylide. Preferred reducing agents include sodium bis(2-methoxyethoxy) aluminum hydride (Red Al®). Preferably, about 100 to 200% by mole of the alkylating agent should be reacted with the catalyst in order for activation to occur. More preferably, titanocene dichloride requires about 200% by mole of alkylating agent while titanocene monochloride requires about 100% by mole. The activation of such catalysts by reaction with an alkylating agent is further described and illustrated in the examples.

Metal alkoxide and metal aryloxide catalysts are air stable, and are self-activating in the presence of a silane.

One skilled in the art will appreciate that a variety of solvents can be used with these catalysts. One general requirement of a suitable solvent is that the catalyst must be completely or partially soluble within the solvent. Complete solubility is not required as there need only be enough catalyst present in the solution to facilitate a reaction Exemplary solvents include tetrahydrofuran, toluene, benzene, hexane, ether and the like. An additional advantage of the invention is that the substrate may be present in the organic solvent at relatively high concentrations (e.g., about 1M), thus enabling smaller reactors to be used and less waste solvent to be generated. It is noted that no solvent other than the silane itself may be required.

As noted above, the reducing reagent preferred in the present processes is a silane compound which must be capable of supplying a hydride ion during the reduction reaction. Exemplary silane compounds which may be used in these processes are represented by the formulas shown below.

$$R(R')SiH_2 \quad (I)$$

$$RSiH_3 \quad (II)$$

$$RO(R'O)SiH_2 \quad (III)$$

$$\begin{array}{c} (OR'') \\ | \\ (RO)-Si-H \\ | \\ (OR') \end{array} \quad (IV)$$

$$\begin{array}{c} R \quad R \quad R \\ | \quad | \quad | \\ Me_3SiO-Si-(O-Si-O)_n-Si-OSiMe_3 \\ | \quad | \quad | \\ H \quad H \quad H \end{array} \quad (V)$$

where R, R' and R" represent hydride, alkyl, aryl or hydride groups and may be the same or different. Specific examples of suitable silane reducing reagents include silane, diphenylsilane, phenylsilane, diethylsilane, dimethylsilane and triethoxysilane, trimethoxysilane, and poly(methylhydrosiloxane).

Preferably, the silane compound, when used as the reducing reagent, is present in an amount ranging from about 100 to about 300% by mole as compared to the amount of the substrate. Where the reducing agent is hydrogen the silane can be present at about 0.1 to 5 equivalents, and more preferably 0.1-2.5 equivalents, relative to the catalyst.

One aspect of the invention, as noted above, involves the catalytic asymmetric reduction of imines, oximes, hydrazones, and the like to yield amines having a high degree of enantiomeric purity. The desired substrate can be reduced to an amine enriched in one enantiomer, using a suitable catalyst of the type described above, which is enriched in one enantiomer. A preferred catalyst is one which is enriched in (R,R)-Ethylene-1,2-bis($\eta^5$-4,5,6,7-tetrahydroindenyl)-titanium (R)-1,1'-binaphth-2,2'-diolate. Preferably, this catalyst contains at least about 80% of the (R,R,R) enantiomer. Another preferred catalyst is one which is enriched in (S,S)-Ethylene-1,2-bis($\eta^5$-4,5,6,7-tetrahydroindenyl) titanium (S)-1,1-binaphth-2,2'-diolate. Preferably, this catalyst contains at least about 80% of the (S,S,S) enantiomer.

The degree of enantiomeric excess ("ee") for the amine reaction product depends on a number of factors including the enantiomeric purity of the catalyst, the specific amine being produced, and reaction conditions. For many compounds produced through this reaction relatively high enantiomeric excess values are obtained. In some instances, the "ee" exceeds 90%.

In addition to the procedure described above, optically active end products may be produced by the alternative procedure described below. According to this embodiment an optically active additive is combined with a catalyst of the type described above, which preferably is achiral, but can also be chiral. The silane and the desired substrate may then be added, together with an inert solvent. The reaction is then commenced either in an inert gas (if the silane serves as the reducing agent) or in a hydrogen atmosphere (if hydrogen serves as the reducing agent). The reaction may be carried out at a temperature ranging from about 25° C. to about 100° C.

Catalysts most preferred for use with this alternative asymmetric reduction technique include metal alkoxides and metal aryloxides such as titanium alkoxides and titanium (IV) aryloxides. Preferably, the catalyst is used in an amount ranging between about 5-10 mole %, relative to the amount of substrate.

Suitable optically active additives include amines, diamines, alcohols, diols, acids, diacids, thiols, and phosphines. Exemplary compounds include (1R, 2R)-diaminocyclohexane; (1S,2S)-diaminocyclohexane; (R)-1, 1'-Bi-2-naphthol, (S) 1, 1'-Bi-2-naphthol; (1R, 2S)-ephedrine; (1S, 2R)-ephedrine; and 1,1,4,4-tetraphenyl-2,3-O-isopropylidene-D-threitol.

This alternative procedure for producing optically active end products can be effected in the following manner. Activation of the catalyst (if necessary) proceeds according to the method described above. Thereafter, approximately 0.1 to 10 mole % of catalyst is combined with about 0.1 to 100 mole % of the chiral additive in an inert solvent. The silane is then added to the mixture at 100 to 300 mole %, followed by the addition of the substrate. The mixture may then be reacted, at a temperature between about 25° C. to 100° C. This reaction may be carried out in an inert gas such as argon or nitrogen, using the silane compound as the reducing agent. Alternatively, the reaction may be carried out in hydrogen, using hydrogen as the reducing agent.

The order in which the catalyst and reactants are combined is not believed to be critical. The chiral additive and silane reductant may be combined first followed by the addition of catalyst and then substrate. Also, the catalyst and silane reductant may be combined first, followed by the addition of chiral additive and then substrate. The catalyst and chiral additive may also be combined first, followed by the addition of silane reductant and then substrate.

In the above description, the mole percent is relative to the amount of substrate unless otherwise noted. Moreover, one skilled in the art will understand that inert solvents include, by way of example, tetrahydrofuran, toluene, hexane, benzene, and ether.

The non-asymmetric reduction of imine, oxime, hydrazone, oxime 0-alkylether, oxime O-arylether, N,N-dialkylhydrazone, N,N-diarylhydrazone, and N-alkyl-N-arylhydrazone substrates proceeds generally as described above, and preferably, using an achiral catalyst.

This reduction reaction is further described in the examples which follow.

EXAMPLE I

Asymmetric Reduction of acetophenone N-methyl imine to N-methyl-1-phenylethylamine (R,R)-Ethylene-1,2-bis($\eta^5$-4,5,6,7-tetrahydroindenyl) titanium (R)-1,1'-binaphth-2,2'-diolate (53 mg, 0.089 mmol) was dissolved in 4 mL of dry benzene in a Schlenk tube under a nitrogen atmosphere. The tube was wrapped in aluminum foil. A solution of n-butyllithium (72 µL, 0.12 mmol, 1.6M in hexane) was added and the mixture was shaken until it turned a dark red brown color. After 5 min. phenylsilane, (164 µL, 1.33 mmol) was added and the reaction mixture turned blue, then brown, in color. After 10 minutes acetophenone N-methyl imine (119 mg, 0.89 mmol) was added. The tube was shaken and left for about 20 hours at room temperature. The resulting solution was diluted with 15 mL of ether and 3 mL of methanol and allowed to stir for 2 hours. The reaction mixture was then washed with 10 mL of water and extracted with 1M HCl (2×10 mL). The aqueous layer was separated, basified with 5M NaOH (until strongly basic to pH paper), and extracted with ether (3×20 mL). The ether solution was dried over anhydrous sodium sulfate and concentrated to yield 60 mg (0.45 mmol, 50% yield) of N-methyl-1-phenylethylamine as a yellow oil. The yield for repeated experiments ranged from 50 to 80%.

The enantiomeric excess of the amine so isolated was determined by dissolving the amine (10 mg, 0.074 mmol) in 600 µL CDCl$_3$, and then adding triethylamine (19 µL, 0.14 mmol) followed by (S)-α-methoxy-α-(trifluoromethyl)phenylacetyl chloride (16 µL, 0.083 mmol). Integration of the N-methyl peaks in the $^1$H NMR spectrum showed a 97% diastereomeric excess for the amide (the peaks were compared to those in the spectrum of the amide prepared in the same manner by the reaction of racemic amine and (S)-α-methoxy-α-(trifluoromethyl) phenylacetyl chloride). The diastereomeric excess for repeated experiments ranged from 97-99%. This indicates that the enantiomeric excess of the amine produced in this procedure is 97-99%.

EXAMPLE II

Asymmetric Reduction of indanone N-methyl imine to N-methyl-1-indanamine (R,R)-Ethylene-1,2-bis($\eta^5$-4,5,6,7-tetrahydroindenyl) titanium (R)-1,1'-binaphth-2,2'-diolate (30 mg, 0.050 mmol) was dissolved in 4 mL of dry benzene in a Schlenk tube under a nitrogen atmosphere. The tube was wrapped in aluminum foil. A solution of n-butyllithium (41 µL, 0.065 mmol, 1.6M in hexane) was added and the mixture was shaken until it turned a dark red brown color. After 5 min. phenylsilane, (93 µL, 0.75 mmol) was added and the reaction mixture turned blue, then brown, in color. After 10 min. indanone N-methyl imine (72.6 mg, 0.50 mmol) was added. The tube was shaken and left for about 20 hours at room temperature. The resulting solution was diluted with 15 mL of ether and 3 mL of methanol and allowed to stir for 2 hours. The reaction mixture was then washed with 20 mL of water and extracted with 1M HCl (2×20 mL). The aqueous layer was separated, basified with 5 M NaOH (until strongly basic to pH paper), and extracted with ether (2×50 mL). The ether solution was dried over anhydrous sodium sulfate and concentrated to yield 65 mg (0.44 mmol, 88% yield) of N-methyl-1-indanamine as a yellow oil.

The enantiomeric excess of the amine so isolated was determined by dissolving the amine (10 mg, 0.074 mmol) in 600 μL CDCl₃, and then adding triethylamine (19 μL, 0.14 mmol) followed by (S)-α-methoxy-α-(trifluoromethyl)phenylacetyl chloride (16 μL, 0.083 mmol). Integration of the proton peaks on C-1 in the ¹H NMR spectrum showed a 70% diastereomeric excess for the amide (the peaks were compared to those in the spectrum of the amide prepared in the same manner from racemic amine and (S)-α-methoxy-α-(trifluoromethyl) phenylacetyl chloride). This indicates that the enantiomeric excess of the amine produced in this procedure is 70%.

EXAMPLE III

Reduction (in hydrogen atmosphere) of acetophenone N-benzyl imine to N-benzyl-1- phenylethylamine In a dry Schlenk tube under argon was placed (R,R)-Ethylene-1,2-bis(η⁵-4,5,6,7-tetrahydroindenyl) titanium (R)-1,1'-binaphth-2,2'-diolate (25 mg, 0.042 mmol) and THF (4 mL). A solution of n-butyllithium (53 μL, 0.084 mmol, 1.6M in hexane) was added and the mixture was stirred for 10 minutes, at which time the color was a dark shade of brown. Phenylsilane (13 μL, 0.105 mmol) was then added and the mixture was stirred for another 10 minutes, the color changing to a darker shade of brown. Acetophenone N-benzyl imine (87 mg, 0.42 mmol) was then added and the reaction vessel was sealed and moved to a dry box. The reaction mixture was transferred to a Parr high pressure reactor, which was sealed and removed from the dry box. The reactor was charged with hydrogen to 1900 psi and heated to 65° C. After stirring for 48 hours the mixture was opened to air and concentrated. The residue was diluted with diethyl ether (20 mL) and extracted with 1N HCl (3×10 mL). The combined aqueous layers were basified with NaOH until strongly basic to pH paper and extracted with diethyl ether (4×25 mL). The organic layers were combined, dried over sodium sulfate and concentrated to produce 82–89% yield of N-benzyl-1-phenylethylamine. The enantiomeric excess (ee), as determined by HPLC analysis of the free amine using a Chiralcel OD column, was 89–92% in favor of the (R)-enantiomer.

EXAMPLE IV

Asymmetric Reduction (in Hydrogen) of 2-acetylfuran N-benzyl imine to N-benzyl-1-(2-furyl)-ethylamine The procedure of Example III was followed to reduce 2-acetylfuran N benzyl imine (84 mg, 0.42 mmol). This reaction yielded N-benzyl-1-(2-furyl)-ethamine at 71–84% yield and 26–43% ee as determined in Example III.

EXAMPLE V

Asymmetric Reduction (in Hydrogen) of 2-hexanone N-benzyl imine to N-benzyl-2-hexylamine The procedure, of Example III was followed to reduce 2-hexanone N-benzyl imine (80 mg, 0.42 mmol). This reaction N-benzyl-2-hexylamine at 63–97% yield and 56–62% ee as determined in Example III.

EXAMPLE VI

Asymmetric Reduction (in Hydrogen) of 2-phenyl-3,4-dihydro-5H-pyrrole to 2-phenyl-pyrrolidine The procedure of Example III was followed to reduce 2-phenyl-3,4-dihydro-5H-pyrrole (61 mg., 0.42 mmol). The reaction yielded 2-phenylpyrrolidine at 82% yield and 92–96% ee a determined by GLC of the Mosher Amides (prepared as described in Example I) using a Cyclodex B column.

With respect to the above examples, it is noted that the reactions were run under an atmosphere of nitrogen, argon or hydrogen. Further, the tetrahydrofuran, diethyl ether and benzene used in the examples were distilled under argon from sodium/benzophenone ketyl before use. The titanocene dichloride was Purchased from Boulder Scientific Inc. of Mead, Colo., and was used without further purification. The (R,R)-Ethylene-1,2-bis(η⁵-4,5,6,7-tetrahydroindenyl) titanium (R)-1,1'-binaphth-2,2'-diolate catalyst was prepared according to the process of Wild et al., *J. Organomet. Chem.*, 1982, 232, 233.

The imine substrates were prepared according to standard procedures known in the art.

The above examples are intended to be illustrative of the invention and should not be read to limit the invention to the specific reduction reactions provided in the examples. One skilled in the art will readily appreciate that the invention is applicable to a variety of reduction reactions in which the substrate is an imine and that a variety of catalysts may be used in these reduction reactions.

What is claimed is:

1. A catalytic asymmetric reduction process, comprising the steps of:
providing a catalytic amount of an active species of an enantiomerically enriched chiral catalyst selected from the group consisting of M(L)(L')(L''), M(L)(L')(L'')(L'''), M(L)(L')(L'')(L''') (L$^{iv}$), and M(L)(L')(L'')(L''')(L$^{iv}$)L$^{v}$), where M is a group 3, 4, 5 or 6 metal, a lanthanide or an actinide, and L, L', L'', L''', L$^{iv}$, L$^{v}$, independently, is some combination of H, alkyl, aryl Si(R)(R')(R''), halogen, —OR, —SR, or —NR(R'), or a cyclopentadienyl group having the formula

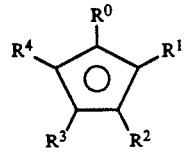

where R, R', and R'' is H, alkyl, or aryl and may be different or the same, and where R⁰, R¹, R², R³, and R⁴ are hydrogen, alkyl, aryl, trialkylsilyl, triarylsilyl, (dialkyl)arylsilyl, or (diaryl)alkylsilyl groups in any combination:
adding a silane compound to the catalyst;
reacting a substrate, selected from the group consisting of imines, oximes, hydrazones, oxime O-alkyl ethers, oxime O-aryl ethers, N,N-dialkylhydrazones, N,N-diarylhydrazones, and N-alkyl-N-arylhydrazones, in the presence of said catalyst and the silane compound; and recovering and purifying an amine reaction product having a high level of enantiomeric purity.

2. The process of claim 1 wherein the enantiomerically enriched chiral catalyst is a titanium-containing catalyst selected from the group consisting of L(L')(L")Ti; L(L')(L")(L''')Ti, L(L')Ti—X; L(L')(L")Ti—X; L(L')Ti—X$_2$; L(L')Ti—H; and L(L')(L")TiH where X is a halogen, and where L, L', L" and L''' are —OR, —SR, —NR(R'), R, or a cyclopentadienyl group of the structure

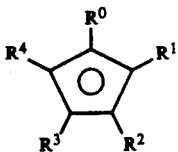

where R and R' are an alkyl, hydride, aryl, or silyl group, and $R^0$, $R^1$, $R^2$, $R^3$ and $R^4$ are hydrogen, alkyl, aryl, trialkylsilyl, triarylsilyl, (dialkyl)arylsilyl, or (diaryl)alkylsilyl groups in any combination.

3. The process of claim 2 wherein the catalyst is an enantiomerically enriched chiral bis(cyclopentadienyl) titanium complex.

4. The process of claim 3 wherein the catalyst is an enantiomerically enriched chiral complex selected from the group consisting of chiral bis(cyclopentadienyl) titanium monohalide complexes, chiral bis(cyclopentadienyl) titanium monoalkoxide complexes, chiral bis(cyclopentadienyl) titanium dihalide complexes, chiral bis(cyclopentadienyl) titanium dialkoxide complexes, and chiral bis(cyclopentadienyl) titanium diaryloxide complexes.

5. The process of claim 4 wherein the catalyst is enantiomerically enriched with a compound selected from the group consisting of (R,R)-Ethylene-1,2-bis ($\eta^5$-4, 5, 6, 7-tetrahydroindenyl) titanium (R)-1,1'-binaphth-2,2'-diolate; or (S,S)-Ethylene-1,2-bis ($\eta^5$-4,5,6,7-tetrahydroindenyl) titanium (S)-1,1'-binaphth-2,2'diolate.

6. The process of claim 1 wherein the silane compound is selected from the group consisting of silane, diphenylsilane, phenylsilane, diethyl silane, dimethylsilane. triethoxysilane, trimethoxysilane and poly(methylhydrosiloxane).

7. The process of claim 1 wherein the catalyst is present in an amount ranging between about 2.5 and 10 percent by mole.

8. The process of claim 5 wherein an enantiomerically enriched quantity of the catalyst constitutes in excess of 80% of one enantiomer of the catalyst.

9. The process of claim 1 wherein following the step of reacting the substrate in the presence of the catalyst and the silane compound, the process further includes the step of cleaving silicon from the resulting reaction product.

10. The process of claim 4 wherein the chiral bis(cyclopentadienyl) titanium monohalide, chiral bis(cyclopentadienyl) titanium monoalkoxide, chiral bis(cyclopentadienyl) titanium dihalide and chiral bis(cyclopentadienyl) titanium dialkoxide complexes are activated as catalysts by reaction with an alkylating or reducing agent.

11. The process of claim 10 wherein the alkylating agent is selected from the group consisting of n-butyllithium, n-pentylmagnesium bromide, and sodium acetylide.

12. The process of claim 10 wherein the reducing agent is sodium bis(2-methoxyethoxy) aluminum hydride.

13. The process of claim 1 wherein the silane compound is added in a stoichiometric quantity relative to the catalyst.

14. The process of claim 13 wherein the step of reacting the substrate in the presence of the catalyst and silane compound is conducted in an atmosphere of an inert gas.

15. The process of claim 1 wherein the step of reacting the substrate in the presence of the catalyst and silane compound is conducted in a hydrogen atmosphere, where the hydrogen acts as a reducing agent.

16. The process of claim 15 wherein the silane compound is present in the range of 0.1 to 5.0 equivalents relative to the catalyst.

17. The process of claim 15 wherein the step of reacting the substrate in the presence of the catalyst and silane compound, in a hydrogen atmosphere, is conducted in a pressure reactor at a pressure in excess of 1 atmosphere.

18. A process for the catalytic reduction of a substrate to yield an amine, comprising the steps of:

providing a catalytic amount of an active species of a catalyst selected from the group consisting of M(L)(L')(L"), M(L)(L')(L")(L'''), M(L)(L')(L")(L''')(L$^{iv}$), and M(L)(L')(L")(L''') (L$^{iv}$)(L$^v$), where M is a group 3, 4, 5 or 6 metal, a lanthanide or an actinide, and L, L', L", L''', L$^{iv}$, L$^v$, independently, is some combination of H, alkyl, aryl, S(R)(R')(R"), halogen, —OR, —SR, —NR(R'), or a cyclopentadienyl group having the formula

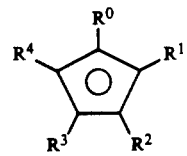

where R, R', and R" is H, alkyl or aryl and may be different or the same, and where $R^0$, $R^1$, $R^2$, $R^3$, and $R^4$ may be hydrogen, alkyl, aryl, trialkylsilyl, triarylsilyl, (dialkyl)arylsilyl, or (diaryl)alkylsilyl groups in any combination;

adding a stoichiometric amount of a silane compound to the catalyst;

reacting a substrate, selected from the group consisting of imines, oximes, hydrazones, oxime O-alkyl ethers, oxime O-aryl ethers, N,N-dialkylhydrazones, N,N-diarylhydrazones, N-alkyl-N-arylhydazones, in the presence of said catalyst and the silane compound; and recovering and purifying an amine reaction product.

19. The process of claim 18 wherein the catalyst is a titanium-containing complex selected from the group consisting of titanocene monochloride and titanocene dichloride.

20. The process of claim 10 wherein said catalyst is a titanium-containing complex selected from the group consisting of L(L')(L")Ti; L(L')(L")(L''')Ti; L(L')Ti—X; L(L')(L")Ti—X; L(L')Ti—X$_2$; L(L')TiH; and L(L')(L")TiH where X is a halogen, and where L, L', L" and L''' can be —OR, —SR, —NR(R'), R, or a cyclopentadienyl group of the structure

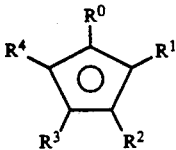

where R and R' can be an alkyl, aryl, hydride or silyl group, and $R^0$, $R^1$, $R^2$, $R^3$ and $R^4$ can be hydrogen, alkyl, aryl, trialkylsilyl, triarylsilyl, (dialkyl)arylsilyl, or (diaryl)alkylsilyl groups in any combination.

21. The process of claim 20 wherein active species of titanium monochloride and titanium dichloride catalysts are generated by reaction with an organometallic alkylating agent or a reducing agent.

22. The process of claim 21 wherein the organometallic alkylating agent is selected from the group consisting of n-butyllithium, n-pentylmagnesium bromide, and sodium acetylide.

23. The process of claim 21 wherein the organometallic alkylating agent is sodium bis(2-methoxyethoxy) aluminum hydride.

24. The process of claim 18 wherein the silane compound is selected from the group consisting of silane, diphenylsilane, phenylsilane, diethylsilane, dimethylsilane, triethoxysilane, trimethoxysilane, and poly(methylhydrosiloxane).

25. The process of claim 18 wherein the catalyst is present in an amount ranging between about 2.5 and 10 percent by mole, relative to the amount of substrate.

26. The process of claim 18 wherein following the step of reacting the substrate in the presence of the catalyst and the silane compound, the process further comprises the step of cleaving silicon from the resulting reaction product.

27. A catalytic asymmetric reduction process, comprising the steps of:
providing a mixture of (i) a catalytic amount of an active species of a catalyst selected from the group consisting of M(L)(L')(L'')(L''), M(L)(L')(L'')(L'''), M(L)(L')(L'')(L''')(L$^{iv}$), and M(L)(L')(L'')(L''')(L$^{iv}$)(L$^v$), where M is a group 3, 4, 5 or 6 metal, a lanthanide or an actinide, and L, L', L'', L''', L$^{iv}$, L$^v$, independently, is some combination of H, alkyl, aryl, Si(R)(R')(R''), halogen, —OR, —SR, —NR(R'), or a cyclopentadienyl group having the formula

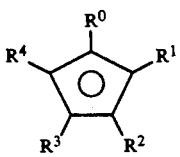

where R, R', and R'' is H, alkyl, or aryl and may be different or the same, and where $R^0$, $R^1$, $R^2$, $R^3$, and $R^4$ may be hydrogen, alkyl, aryl, trialkylsilyl, triarylsilyl, (dialkyl)arylsilyl, or (diaryl)alkylsilyl groups in any combination; (ii) a chiral additive; and (iii) a silane compound able to supply a hydride ion during the reduction reaction;
reacting a substrate, selected from the group consisting of imines, oximes, hydrazones, oxime O-alkyl ethers, oxime O-aryl ethers, N,N-dialkylhydrazones, N,N-diarylhydrazones, and N-alkyl-N-arylhydrazones, with the mixture; and
recovering and purifying an amine reaction product enriched in one enantiomer.

28. The process of claim 27 wherein the catalyst is selected from the group consisting of metal alkoxides and metal aryloxides.

29. The process of claim 28 wherein the catalyst is selected form the group consisting of titanium (IV) isopropoxide, trichlorotitanium (IV) isopropoxide, titanium (IV) ethoxide, titanium (IV) methoxide, titanium (IV) propoxide and titanium (IV)butoxide.

30. The process of claim 27 wherein the silane compound is selected from the group consisting of silane, diphenylsilane, phenylsilane, diethylsilane, dimethylsilane, triethoxysilane, trimethoxysilane and poly(methylhydrosiloxane).

31. The process of claim 27 wherein the catalyst is present in an amount ranging between about 2.5 and 10 mole %, relative to the amount of substrate.

32. The process of claim 27 wherein the chiral additive is present in an amount ranging between about 0.1 and 100 mole %, relative to the amount of substrate.

33. The process of claim 32 wherein the chiral additive is selected from the group consisting of (1R, 2R)-diaminocyclohexane; (1S, 2S)-diaminocyclohexane; (R)-1, 1'-Bi-2-naphthol, (S)1, 1'-Bi-2-naphthol; (1R,2S)-ephedrine; (1S, 2R)-ephedrine; and 1,1,4,4-tetraphenyl-2,3-O-isopropylidene-D-threitol.

34. The process of claim 27 wherein following the step of reacting the substrate in the presence of the mixture, the process further includes the step of cleaving silicon from the resulting reaction product.

35. The process of claim 27 wherein the silane compound is added in a stoichiometric quantity relative to the catalyst.

36. The process of claim 35 wherein the step of reacting the substrate in the presence of the catalyst and silane compound is conducted in an atmosphere of an inert gas.

37. The process of claim 29 wherein the step of reacting the substrate in the presence of the mixture is conducted in a hydrogen atmosphere, where the hydrogen acts as a reducing agent.

38. The process of claim 37 wherein the silane compound is present in the range of 0.1 to 5.0 equivalents relative to the catalyst.

39. The process of claim 38 wherein the step of reacting the substrate in the presence of the mixture in a hydrogen atmosphere is conducted in a pressure reactor at a pressure in excess of 1 atmosphere.

40. A catalytic asymmetric reduction process, comprising the steps of:
providing a catalytic amount of an active species of an enantiomerically enriched chiral catalyst selected from the group consisting of M(L)(L')(L''), M(L)(L')(L'')(L'''), M(L)(L')(L'')(L''')(L$^{iv}$), and M(L)(L')(L'')(L''')(L$^{iv}$)(L$^v$), where M is a group 3, 4, 5 or 6 metal, a lanthanide or an actinide, and L, L', L'', L''', L$^{iv}$, L$^v$, independently, is some combination of H, alkyl, aryl, Si(R)(R')(R''), halogen, —OR, —SR, or —NR(R'), or a cyclopentadienyl group having the formula

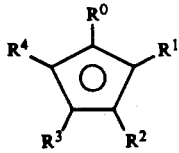

where R, R', and R" are H, alkyl, aryl, and may be different or the same, and where $R^0$, $R^1$, $R^2$, $R^3$, and $R^4$ is hydrogen, alkyl, aryl, trialkylsilyl, triarylsilyl, (dialkyl)arylsilyl, or (diaryl)alkylsilyl groups in any combination;

reacting a substrate, selected from the group consisting of imines, oximes, hydrazones, oxime O-alkyl ethers, oxime O-aryl ethers, N,N-dialkylhydrazones, N,N-diarylhydrazones, and N-alkyl-N-arylhydrazones in a hydrogen atmosphere in the presence of said catalyst, where hydrogen serves as the reducing agent; and recovering and purifying an amine reaction product having a high level of enantiomeric purity.

41. A process for the catalytic reduction of a substrate to yield an amine, comprising the steps of:

providing a catalytic amount of an active species of a non-macrocyclic metal catalyst selected from the group consisting of $M(L)(L')(L\Delta)$, $M(L)(L')(L'')(L''')$, $M(L)(L')(L'')(L''')(L^{iv})$, and $M(L)(L')(L''')(L^{iv})(L^v)$, where M is a group 3, 4, 5 or 6 metal, a lanthanide or an actinide, and L, L', L'', L''', $L^{iv}$, $L^v$, independently, is some combination of H, alkyl, aryl, $Si(R)(R')(R'')$, halogen, —OR, —SR, —NR(R'), or a cyclopentadienyl group having the formula

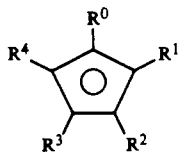

where R, R', and R" are H, alkyl or aryl and may be different or the same, and where $R^0$, $R^1$, $R^2$, $R^3$, and $R^4$ is hydrogen, alkyl, aryl trialkylsilyl, triarylsilyl, (dialkyl)arylsilyl, or (diaryl)alkylsilyl groups in any combination;

reacting a substrate, selected from the group consisting of imines, oximes, hydrazones, oxime O-alkyl ethers, oxime O-aryl ethers, N,N-dialkylhydrazones, N,N-diarylhydrazones, and N-alkyl-N-arylhydrazones in a hydrogen atmosphere in the presence of said catalyst, wherein hydrogen serves as the reducing agent;

recovering and purifying an amine reaction product.

42. A catalyst asymmetric reduction process, comprising the steps of:

providing a mixture of (i) a catalytic amount of an active species of a catalyst selected from the group consisting of $M(L)(L')(L'')$, $M(L)(L')(L'')(L''')$, $M(L)(L')(L'')(L''')(L^{iv})$, and $M(L)(L')(L'')(L''')(L^{iv})(L^v)$, where M is a group 3, 4, 5 or 6 metal, a lanthanide or an actinide, and L, L', L'', L''', $L^{iv}$, $L^v$, independently, is some combination of H, alkyl, aryl, $Si(R)(R')(R'')$, halogen, —OR, —SR, —NR(R'), or a cyclopentadienyl group having the formula

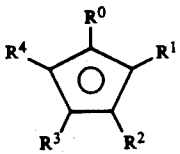

where R, R', and R" are H, alkyl or aryl and may be different or the same, and where $R^0$, $R^1$, $R^2$, $R^3$, and $R^4$ is hydrogen, alkyl, aryl, trialkylsilyl, triarylsilyl, (dialkyl)arylsilyl, or (diaryl)alkylsilyl groups in any combination; and (ii) a chiral additive;

reacting a substrate, selected from the group consisting of imines, oximes, hydrazones, oxime O-alkyl ethers, oxime O-aryl ethers, N,N-dialkylhydrazones, N,N-diarylhydrazones, and N-alkyl-N-arylhydrazones, with the mixture in a hydrogen atmosphere where hydrogen serves as the reducing agent; and recovering and purifying an amine reaction product enriched in one enantiomer.

43. The process of claim 27 wherein the chiral additive is selected from the group consisting of amines, diamines, alcohols, diols, organic acids, organic diacids, thiols, and phosphines.

44. The process of claim 42 wherein the chiral additive is selected from the group consisting of amines, diamines, alcohols, diols, organic acids, organic diacids, thiols, and phosphines.

45. The process of claim 18 wherein the step of reacting the substrate in the presence of the catalyst and silane compound is conducted in a hydrogen atmosphere, where the hydrogen acts as a reducing agent.

* * * * *

UNITED STATES PATENT AND TRADEMARK OFFICE
CERTIFICATE OF CORRECTION

PATENT NO. : 5,292,893
DATED : March 8, 1994
INVENTOR(S) : Stephen L. Buchwald and Christopher A. Willoughby It is certified that error appears in the above-identified patent and that said Letters Patent is hereby corrected as shown below:

Column 2, line 39, replace "Product" with --product--.

Column 6, line 12, replace "reaction Exemplary" with --reaction. Exemplary--.

Column 10, line 62, replace "catalyst;" with --catalyst:--.

In claim 27, column 13, line 42, replace "consisting of M(L)(L')(L")(L")," with --consisting of M(L)(L')(L"),--.

In claim 37, column 14, line 44, replace "The process of claim 29" with --The process of claim 27--.

In claim 41, column 15, line 27, replace "(LΔ)," with --(L"),--.

Signed and Sealed this

Twenty-fifth Day of October, 1994

Attest:

BRUCE LEHMAN

Attesting Officer     Commissioner of Patents and Trademarks